(12) United States Patent
Basiony

(10) Patent No.: US 11,957,819 B2
(45) Date of Patent: Apr. 16, 2024

(54) ARTIFICIAL KIDNEY TO SUPPORT A CONCEPT OF DIGITAL DIALYSIS (CDD)

(71) Applicant: Mohamed A Basiony, Kenmore, WA (US)

(72) Inventor: Mohamed A Basiony, Kenmore, WA (US)

( * ) Notice: Subject to any disclaimer, the term of this patent is extended or adjusted under 35 U.S.C. 154(b) by 0 days.

(21) Appl. No.: 17/947,110

(22) Filed: Sep. 17, 2022

(65) Prior Publication Data

US 2023/0108191 A1    Apr. 6, 2023

Related U.S. Application Data

(60) Provisional application No. 63/251,661, filed on Oct. 3, 2021.

(51) Int. Cl.
| | | |
|---|---|---|
| *A61M 25/00* | (2006.01) | |
| *A61M 1/14* | (2006.01) | |
| *A61M 1/16* | (2006.01) | |
| *A61M 25/14* | (2006.01) | |

(52) U.S. Cl.
CPC .......... *A61M 1/1696* (2013.01); *A61M 1/155* (2022.05); *A61M 1/1672* (2014.02)

(58) Field of Classification Search
CPC .. A61M 1/1696; A61M 1/155; A61M 1/1672; A61M 1/342; A61M 1/3643; A61M 1/3661; A61M 1/1678; A61M 1/285; A61M 25/0026
See application file for complete search history.

(56) References Cited

U.S. PATENT DOCUMENTS

| | | | | |
|---|---|---|---|---|
| 6,805,683 | B1 * | 10/2004 | Johansson | A61B 5/14528 604/4.01 |
| 2008/0009784 | A1 * | 1/2008 | Leedle | A61M 1/3661 604/43 |
| 2008/0312578 | A1 * | 12/2008 | DeFonzo | A61M 25/0032 604/6.16 |

* cited by examiner

*Primary Examiner* — Pranav N Patel

(57) ABSTRACT

An artificial kidney and its supportive device comprising a catheter having an internal semipermeable membrane tube to act as an artificial kidney. Said catheter comprising a proximal portion having a semipermeable membrane tube, a blood/infusion lumen, a dialysate lumen and side holes, while a distal portion having a dual septa port assembly. Said supportive device comprising a device house with its cover that covers its internal cavity that includes sorbent bags with different sizes and arrangement, a screen, buttons, set knobs, two contactless conductivity cells, bidirectional rotary pumps, rotary valves, pressure sensors, a slot for memory card, a temperature sensor, scales, an IV pole and a blood leak detector.

A method comprising: inserting the catheter having an internal semipermeable membrane tube that acts as artificial kidney into a suitable vein or artery, then using the supportive device to supporting, facilitating, and controlling the operation of the artificial kidney and to managing the dialysate inflow and outflow to and from the dialysate lumen within the catheter and also to managing the blood inflow and outflow to and from the infusate/blood lumen within the catheter to be on opposite direction across the semipermeable membrane of the artificial kidney.

17 Claims, 7 Drawing Sheets

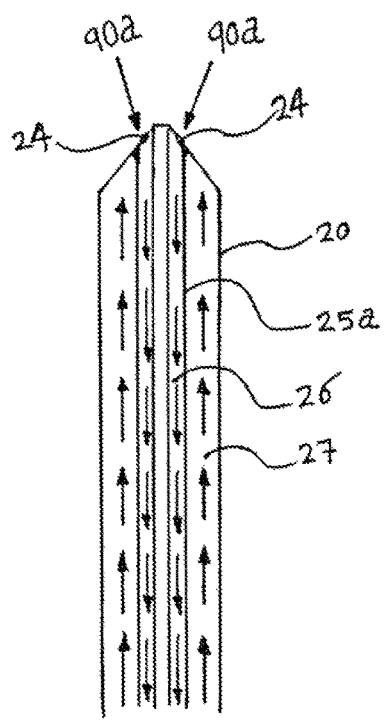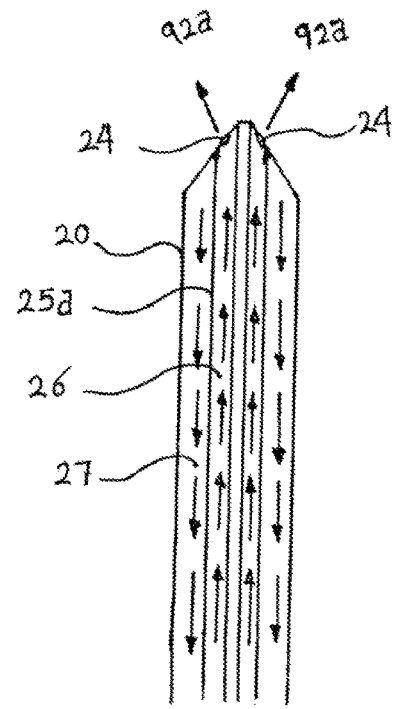
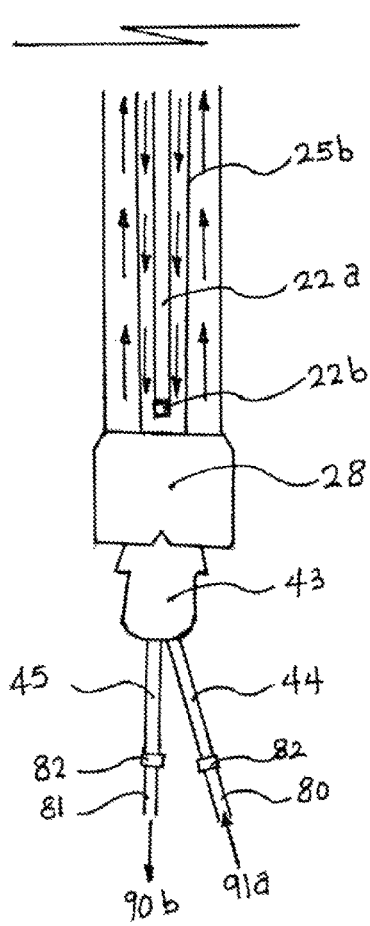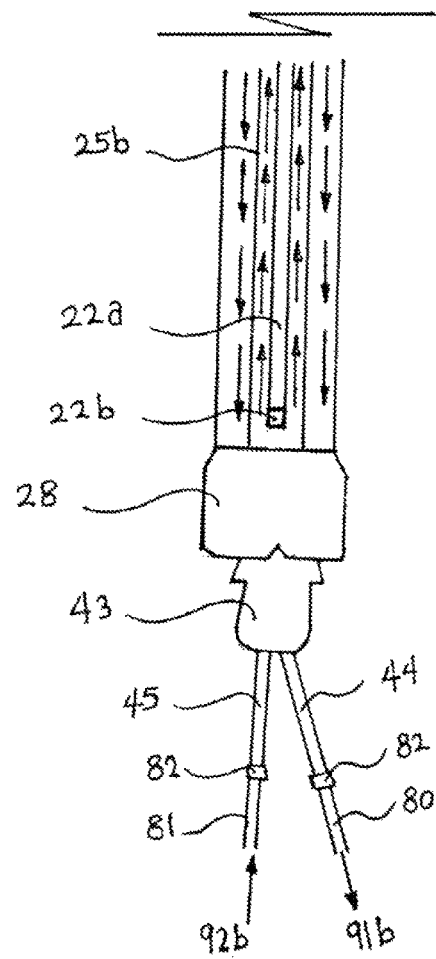
FIG. 6a      FIG. 6b

ARTIFICIAL KIDNEY TO SUPPORT A CONCEPT OF DIGITAL DIALYSIS (CDD)

BACKGROUND

The United States dialysis market stood at USD 90.33 billion in 2019. The rising cases of chronic kidney disorders are expected to boost the visits to the hospitals by patients for procuring renal therapy.

There is a need for a new design to cut the above cost dramatically and to facilitate a home dialysis treatment without compromising a patient safety and dialysis outcome.

SUMMARY

Accordingly, it is an object of the present disclosure to provide an artificial kidney with its supportive device that may combine the features of both a peritoneal dialysis and a hemodialysis. The features of a peritoneal dialysis such as instead of sending a peritoneal solution to a peritoneal cavity, a dialysate solution may be sent to a blood cavity. While the feature of a hemodialysis is that the principal of operation of the present disclosure may be based on a hemodialysis concept as hemodialysis, hemofiltration/hemodiafiltration, isolated ultrafiltration, etc may be run during each dialysis session.

Also, as in a peritoneal dialysis technique, the implemented invention in its operation may support a continuous therapy as ongoing daily dialysis sessions allows for a minimal fluctuation, compared to tiredness after treatment and weakness as next appointment draws close as in a conventional dialysis technique (prior art). Furthermore, there may be no peritonitis, no abdominal muscle weakening, and other problems related to a peritoneal dialysis.

Furthermore, with this implemented invention, there may be no side effects such as muscle cramps, a hypotension, a dizziness, a fatigue, etc. as in a conventional hemodialysis treatment (prior art).

It is still another object to provide an artificial kidney that comprises a catheter with an internal semipermeable membrane tube that may act as an artificial kidney. Said semipermeable tube may have a material that is suitable for a hemodialysis treatment in one implementation. In another implementation, it may have two materials, one material that is suitable for a hemodialysis treatment and another material that is suitable for a hemofiltration/hemodiafiltration treatment and both are connected to each other to support a hemodialysis and a hemofiltration/hemodiafiltration processes during the same dialysis treatment.

It is still another object of this implementation to provide an artificial kidney that comprises a catheter that has been selected for a percutaneous placement directly into an inferior vena cava (IVC) by trans-lumbar approach. In another implementation said catheter may be inserted into an internal jugular, a femoral, a subclavian, or any suitable veins or arteries.

It is still another object of this implementation to provide a supportive device that is used to support, facilitate, and control the operation of said artificial kidney and to monitor the operational parameters. It is also used to warm-up a fresh dialysate bag on a warmer unit and to monitor and control dialysate inflow and outflow during the operation. Said supportive device also has two scales, one to measure a weight of a fresh dialysate bag and a second one to measure a weight of sorbent bags to be able to calculate an actual ultrafiltration during the operation as experts in this industry understand.

It is still another object of this implementation to provide an artificial kidney comprises a catheter that is designed to keep a blood inside a body so there may be no blood related problems that may occur due to a presence of a blood outside a patient's body.

Other features are no blood module to monitor and control the extracorporeal blood, no blood lines and no fistula or graft as in a conventional dialysis system (prior art). Also, no maturation time as said catheter may be used immediately after insertion. Furthermore, there is no fresh dialyzer or recycled dialyzer for each dialysis session.

Further features are no dialysate preparation and monitor unit as in a conventional dialysis system (prior art) as during the operation of the implemented invention a readymade fresh dialysate bag has been used and customized for each patient and there are sorbent bags that have been used to regenerate and refresh a used dialysate solution (spent dialysate). Furthermore, there is no water treatment plant with reverse osmosis module, filters, softeners, etc as in conventional dialysis systems (prior arts).

So, it will be apparent to those skilled in the art that the above features can help to cut current dialysis cost dramatically.

Further feature is said artificial kidney and its supportive device may support the concept of a digital dialysis (CDD) in which a controlled pulsed blood flow and a controlled pulsed dialysate flow are used to maximize the contact time between a blood and a dialysate to enhance the mass transfer across the semipermeable membrane.

Further features are said artificial kidney and its supportive system may have a simple operation technique compared to conventional dialysis machines as in operation, there is just an ON/OFF button, a Test button, a Time button, a Dialysis button, and a Stop button as will be described in a greater detail below.

Further general features such as said artificial kidney and its supportive device may not need an experienced nurse as in conventional dialysis machines to train patients due to its simplicity in operation. Also, furthermore said artificial kidney and its supportive device may not require a hygienic technique and precaution process compared to a conventional peritoneal dialysis technique (prior art).

Further features are said supportive device is a small portable device compared to conventional dialysis machines and it may be wearable. Also, it may run with less technical and operational problems as no fluid enters inside. This may allow for remotely troubleshooting in case of operational and technical errors. These features make said artificial kidney and its supportive device may be suitable for a home treatment so less hospitalization cost. Plus, due to the fact that said supportive device has limited components compared to conventional dialysis machines, so it may have a less manufacturing, maintenance and preventive costs.

Further feature is said supportive device may have a memory card to record conductivity changes, ultrafiltration changes, ammonium levels and other necessary parameters during a dialysis treatment to be uploaded to a dialysis Electronic Medical Record (EMR) to help a dialysis physician to manage, assess and customize the treatment protocol. Furthermore, said artificial kidney and its supportive device have safety sensors for a patient such as pressure sensors, an ammonium level sensor, a blood leak detector, contactless conductivity sensors, a temperature sensor (for a fresh dialysate bag's temperature), etc.

BRIEF DESCRIPTION OF THE DRAWINGS

The accompanying drawings, which are incorporated in, and constitute a part of the specification, illustrate or exemplify embodiment of the present implementation and, together with the description, generally explain the principles and features of the present implementation. The drawings are briefly described as follows:

FIG. 2a is a perspective view of a connection between a semipermeable membrane tube which acts as an artificial kidney and an inner tube of the distal portion of the catheter of FIG. 1;

FIG. 6a illustrates blood flow and dialysate flow directions inside the catheter of FIG. 1 during one phase of operation;

FIG. 6b illustrates blood flow and dialysate flow directions inside the catheter of FIG. 1 during another phase of operation;

DETAILED DESCRIPTION

The following detailed description illustrates the principal of the disclosure by way of example not by way of limitation. Consequently, the scope of the implementation is not to be limited by the field to which the implementation is applied. While a reference use of the present disclosure describes a catheter that has a semipermeable membrane tube (artificial kidney) to be used as an artificial kidney, as those of ordinary skill in the art will readily understand, it will be understood that a catheter with its supportive device may also be used for other types of treatments. The scope of the implementation is not to be limited by the field to which the implementation is applied. Additional non-limiting usage would also include as an example a component such as a port assembly which has a dual septa assembly that can be used as a stand-alone port assembly for other treatments.

Figure 1:
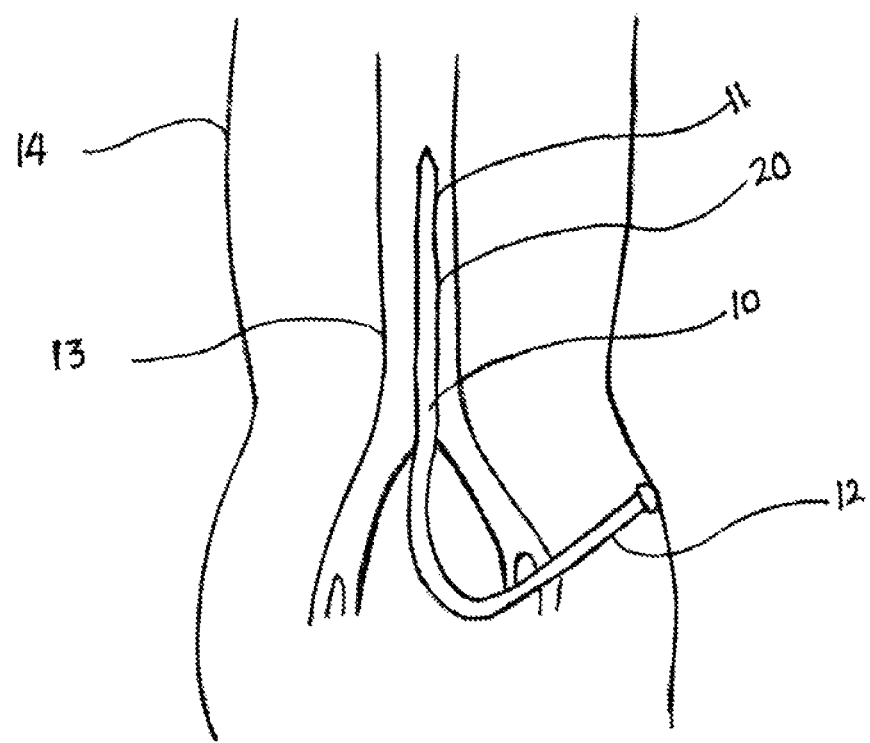
FIG. 1 is a perspective view of the catheter that has an internal semipermeable membrane tube that acts as an artificial kidney after it has been inserted in an inferior vena cava of a patient.

Now referring to FIG. 1, it illustrates a catheter 10, a proximal portion 11 and a distal portion 12. A catheter 10 may be inserted into an inferior vena cava 13 of a patient 14 by a trans-lumbar approach wherein a patient 14 is placed in the left lateral decubitus position under local anesthesia. A catheter 10 has also a catheter body 20 that is made by a biocompatible material such as a polyurethane, a silicon or any other suitable material.

Figure 2:
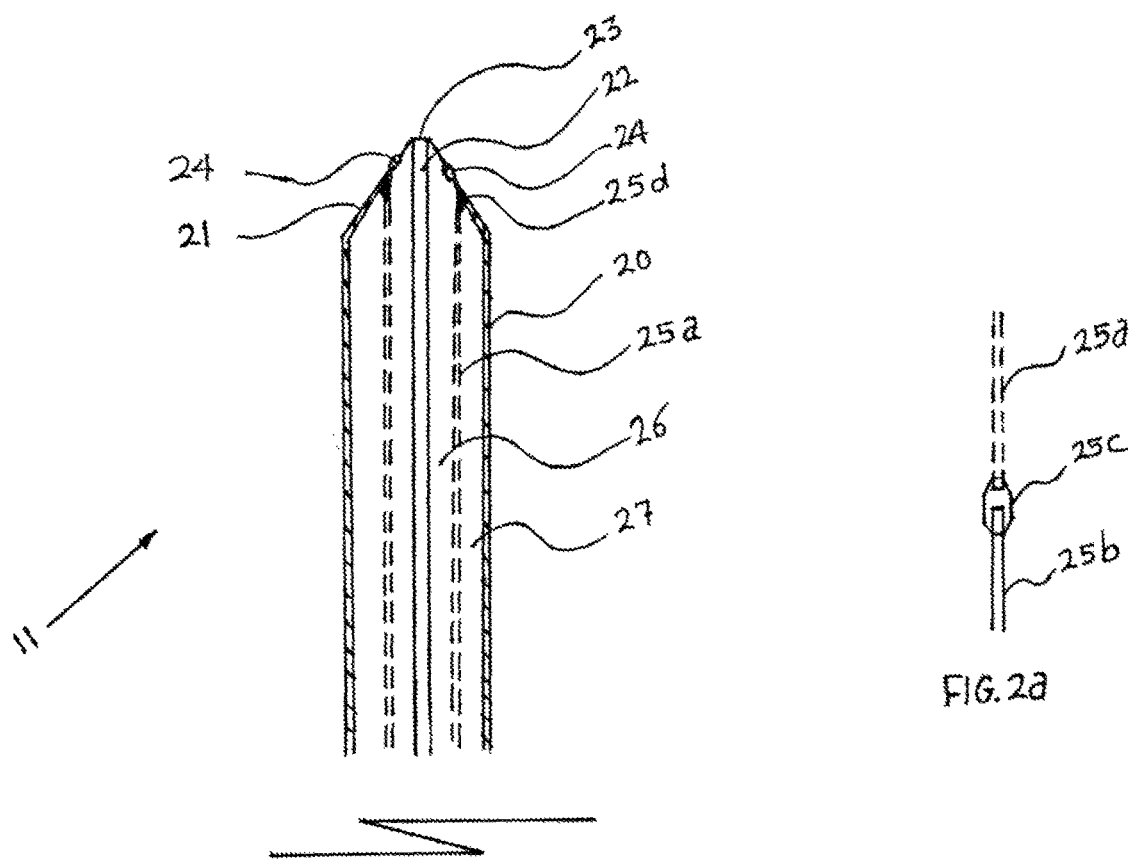
FIG. 2 is a perspective view of the proximal and distal portions of the catheter of FIG. 1.
Figure 2:
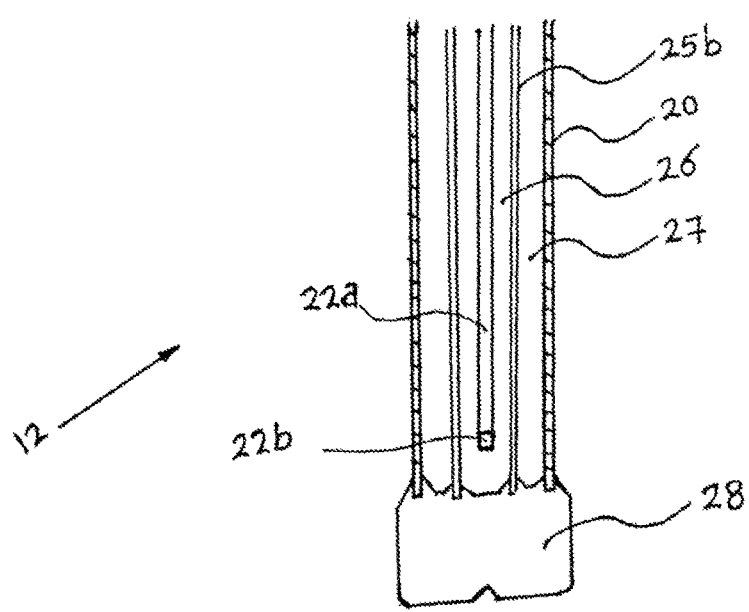

While a reference use of the present disclosure describes a catheter 10 that may be inserted into an inferior vena cava 13, additional non-limiting usage would also include a catheter 10 that may be inserted into an internal jugular vein, a subclavian vein, a femoral vein or any other suitable veins or arteries Now referring to FIG. 2, it illustrates a proximal portion 11 and a distal portion 12 of a catheter 10 wherein a proximal portion 11 comprises: a catheter body 20 that is circular or any suitable shape; a catheter tip 21 that has a tipping configuration for an easy insertion; a guide wire insertion tube 22 that is used during a catheter insertion as in a standard dialysis technique. A guide wire insertion tube 22 is located at the center line of a catheter 10, a self-sealed opening 23 that is self-sealed after an insertion of a catheter 10 inside a vascular access, and side openings 24 that are used for blood inflow and outflow to and from a catheter 10 during the operation.

Also FIG. 2 illustrates a semipermeable membrane tube 25a that acts as an artificial kidney and is located inside a catheter body 20 around a guide wire insertion tube 22 to create a blood/infusate lumen 26, while a dialysate lumen 27 is located between an external surface of a semipermeable membrane tube 25a and an internal surface of a catheter body 20. A distal portion 12 of a catheter 10 comprising: an inner tube 25b that is located inside a catheter body 20 around a distal portion of guide wire insertion tube 22 to create a distal portion of blood/infusate lumen 26, while a distal portion of dialysate lumen 27 is located between an external surface of an inner tube 25b and an internal surface of a distal portion of a catheter body 20. Also, a distal portion 12 comprises a distal portion of guidewire insertion tube 22a with its a block portion 22b that is used to block a distal opening of a distal portion of a guidewire insertion tube 22a after a catheter insertion and before fixing a port assembly 28 on a catheter body 20 by any suitable technique. A semipermeable membrane tube 25a (artificial kidney) is connected to a catheter tip 21 via a suitable connector 25d that is a sealed circular (annular) connector to prevent a blood leak from this area. While an inner tube 25b is also sealed to a port assembly by any suitable seal.

A catheter body 20 has an internal diameter that is in the range from about 5 Fr to about 16 Fr or any suitable diameter. A length of a catheter 10 is in the range of about 15 cm to about 50 cm or any suitable length to suit pediatric and adult applications. While a length of a semipermeable membrane tube 25a (artificial kidney) may represent about 15 to about 95 percentage of the length of a catheter 10 or any suitable percentage. The preferred percentage is from about 70 to 90 percentage. The length of a semipermeable membrane tube 25a must be less than the length of a catheter 10 to avoid a blood leak during the operation. While the length of an inner tube 25b may represent five to ten percentage of the total length of a catheter 10. The preferred length of an inner tube 25b is about 3 to 5 percentage of the total length of a catheter 10.

FIG. 2a, illustrates a connection that is made between a semipermeable membrane tube 25a (artificial kidney) and an inner tube 25b using a suitable connector 25c. A semipermeable membrane tube 25a and an inner tube 25b may have the same diameter which may be a half of a catheter diameter to get the same fluid volume inside both of a blood/infusate lumen 26 and a dialysate lumen 27 during the operation. Or any suitable diameter to maximize the mass transfer across a semipermeable membrane tube 25a (artificial kidney) that is located between a blood/infusate lumen 26 and a dialysate lumen 27.

A semipermeable membrane tube 25a (artificial kidney) is made by any suitable advanced semipermeable membrane that enhances the biocompatibility and minimizes coagulation or the like. On other side an inner tube 25b is made by any suitable material such as a medical polyurethane or silicon or the like and It may not have any pores just a solid tube.

Figure 3A:
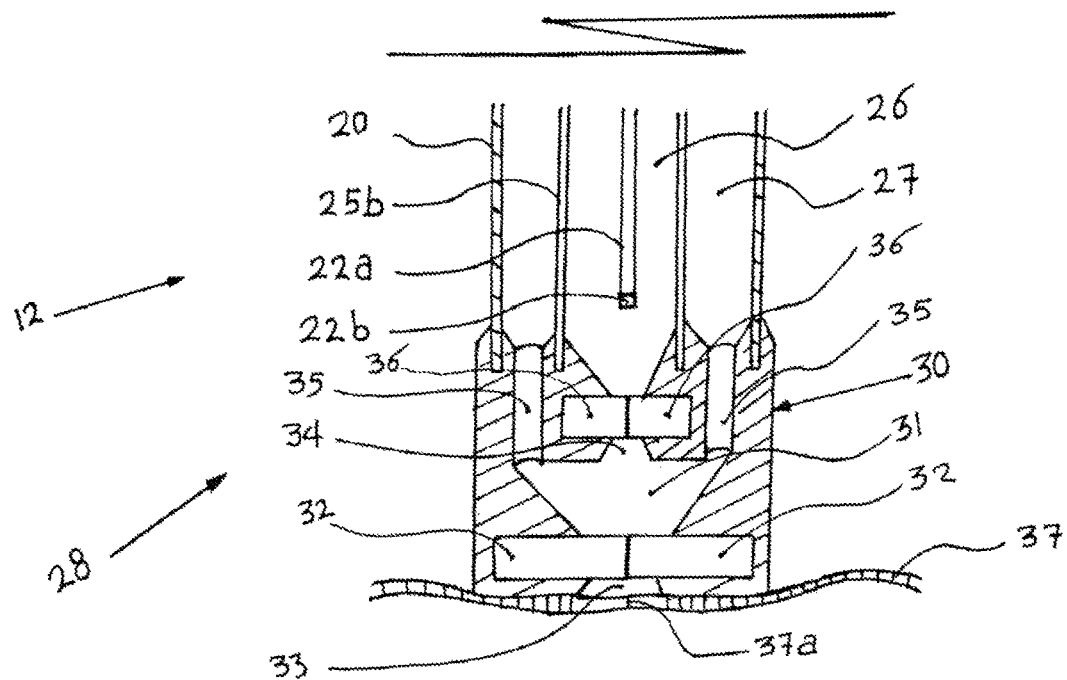
FIG. 3a is a perspective view of the distal portion of the catheter of FIG. 1 with a port assembly that is inserted subcutaneously under a patient's skin.

FIG. 3a illustrates a distal portion 12 of a catheter 10 of FIG. 1 with a port assembly 28 that is inserted subcutaneously under a patient's skin. A port assembly 28 may have dual septa such as a first septum 32 and a second septum 36 to facilitate its operation wherein a port housing 30 that has a cylindrical shape or any suitable shape and is made by a medical PVC or any other suitable material. A port housing 30 is fixed on a distal portion of a catheter body 20 after a catheter insertion by any suitable fixation technique.

FIG. 3a also illustrates a port cavity 31 that has a conical shape or any suitable shape to facilitate a dialysate flow during the operation, a first septum 32 that has a cylindrical shape or any suitable shape and is fixed within a port's housing 30 to prevent a dialysate leakage during the operation as a septum's material is an elastomeric material, an aperture 33 of a first septum 32 is located under a subcutaneous tissue 37 and guided by a tissue tract 37a. An aperture 34 of a second septum 36 is located within a port cavity 31 and dialysate passageways 35 which look like cylindrical tubes within a port housing 30 to facilitate a dialysate inflow and outflow to and from a dialysate lumen 27. As above, a dialysate lumen 27 is located between an external surface of an inner tube 25b and an internal surface of a catheter body 20 while a blood/infusate lumen 26 is located around a distal portion of a guidewire insertion tube 22a and internal surface of an inner tube 25b.

A second septum 36 that looks like a first septum 32 has a cylindrical shape or any suitable shape and is fixed within a port's housing 30 behind a first septum 32 to create a dialysate passageway on both sides internally of a port housing 30. A second septum 36 is used to prevent an infusate or a blood leakage during the operation as a septum's material is an elastomeric material as a first septum 32. In operation an infusate solution from infusate bag 70 is used to be in a direct contact and in a fluid communication with a blood inside a blood/infusate lumen 26 to prevent an air embolism and to push a blood out from a blood/infusate lumen 26 through side openings 24 in one phase of operation and to suck a blood into a blood/infusate lumen 26 through side openings 24 in another phase of operation as below.

Furthermore, FIG. 3a illustrates a subcutaneous tissue 37 and a tissue tract 37a that is alignment with an aperture 33 of a first septum 32 to guide a needle assembly 40 to a port's entrance that is in a line co-incident with the axis of an aperture 33. FIG. 3a also illustrates a distal portion of a guidewire insertion tube 22a and its block portion 22b that is used to block a guidewire insertion tube 22a to prevent a blood or an infusate from entering inside it during the operation. FIG. 3a also illustrates an inner tube 25b and a distal portion of a blood/infusate lumen 26 that is located inside an inner tube 25b around a distal portion of guidewire insertion tube 22a while a distal portion of a dialysate lumen 27 is located between outer surface of an inner tube 25b and an internal surface of a catheter body 20.

Figure 3B:
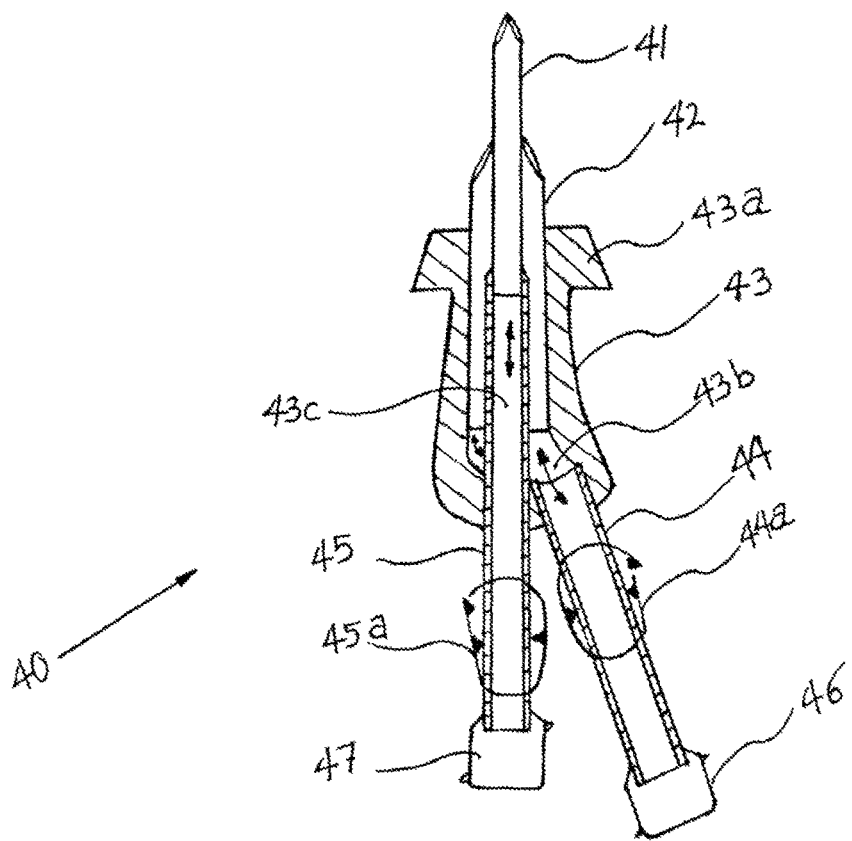
FIG. 3b is a perspective view of a coaxial needle assembly that is used to facilitate fluid inflow and outflow to and from the catheter of FIG. 1.

FIG. 3b illustrates a needle assembly 40 that is used to facilitate inflow and outflow to and from a catheter 10. A needle assembly 40 has a coaxial design wherein a first needle 41 which has a small diameter is positioned inside a second needle 42 which has a large diameter. By this design a user is going to use one needle assembly to be inserted inside an aperture 33 of a first septum 32 and an aperture 34 of a second septum 36 to facilitate inflow and outflow to and from a dialysate lumen 27 and to and from a blood/infusate lumen 26.

Figure 4:
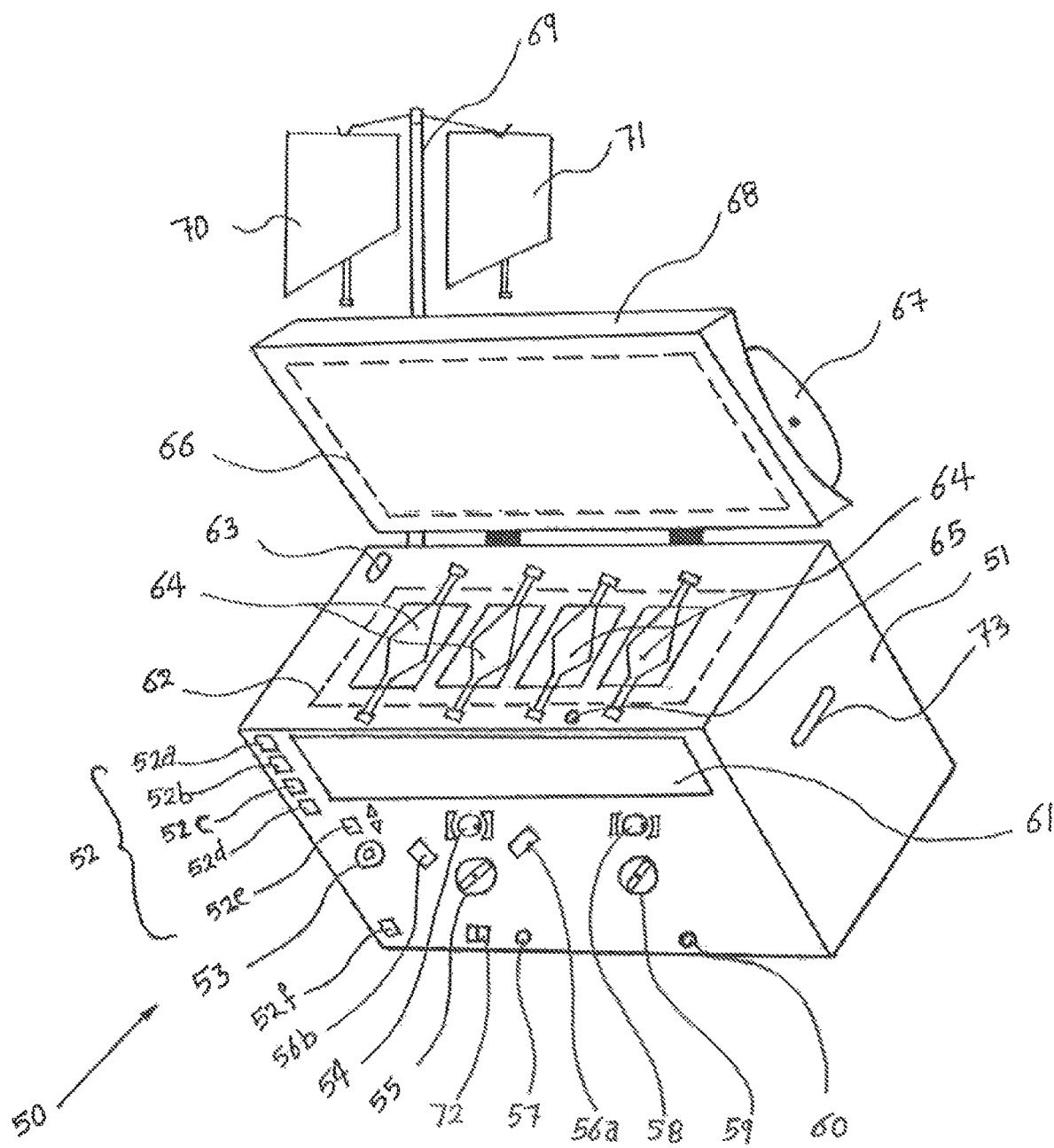
FIG. 4 is a perspective view of the supportive device's components that are used to support, facilitate and control the operation of the catheter and its artificial kidney of FIG. 1 and to monitor the operational parameters.

In operation, a first needle 41 is used to facilitate sucking a blood into a blood/infusate lumen 26 through side openings 24 in one phase of operation and pushing a blood out from a blood/infusate lumen 26 through side openings 24 in another phase of operation using a bi-directional rotary pump2 59 FIG. 4. Doing so, an infusate solution is used from an infusate bag 70 to facilitate a blood inflow and outflow to and from a blood/infusate lumen 26 as an infusate solution is in a fluid communication with a blood inside a blood/infusate lumen 26, so it is used to facilitate sucking of a blood into a blood/infusate lumen 26 in one phase of operation and pushing a blood out from a blood/infusate lumen 26 in another phase of operation using a bi-directional rotary pump2 59.

While a second needle 42 is used to facilitate a dialysate flow from a dialysate bag 67 into a dialysate lumen 27 in one phase of operation and a dialysate flow out from a dialysate lumen 27 in another phase of operation using a bi-directional rotary pump1 55 FIG. 4.

FIG. 3b also illustrates a needle hub 43 with a needle wing 43a which acts as a needle stop after it has been inserted inside a port assembly 28 and is used to fix a needle assembly 40 to a patient's skin during the operation by any suitable fixation technique, a dialysate passageway 43b within a needle hub 43 that is used to facilitate a dialysate inflow and outflow to and from a dialysate lumen 27 as a dialysate passageway 43b is in a fluid communication with a dialysate lumen 27.

FIG. 3b further illustrates an infusate passageway 43c within a needle hub 43 that is used to facilitate an infusate inflow and outflow to and from a blood/infusate lumen 26 as an infusate passageway 43c is in a fluid communication with a blood/infusate lumen 26. Both dialysate passageway 43b and infusate passageway 43c are separated from each other within a needle hub 43 as illustrated in FIG. 3b. Also FIG. 3b illustrates an extension tube 44 with a male connector 46 that is used to connect a needle assembly 40 to the components of a supportive device 50 FIG. 4 that are related to a dialysate side. While an extension tube 45 with a male connector 47 is used to connect a needle assembly 40 to the components of a supportive device 50 that are related to an infusate side. Clamps 44a and 45a are used to clamp extension tubes 44 and 45 whenever is required as in a standard technique.

FIG. 4 illustrates a supportive device 50 that comprises a house 51 with a cover 68. A cover 68 contains a heater to warm up a fresh dialysate bag 67 and a temperature sensor to issue an alarm in case a temperature of the dialysate bag 67 is outside a certain range (both the heater and temperature sensor are not shown for simplicity). During an operation said cover 68 is closed to cover the internal cavity of said device 50 that contains sorbent bags 64 and an ammonium sensor 63. Closing a cover 68 enables an easy access, monitor and deal with said dialysate bag 67 that is located on an external surface of a cover 68 that has a concave shape.

A supportive device 50 also comprises buttons 52 such as an on/off button 52a to open and switch off the device, a test button 52b to test for electronics and sensors before operation, a dialysis button 52c to start a dialysis session, a stop button 52d to end a dialysis session in case a user does not use a time button 52e, a time button 52e is used to set-up the time of operation (associated with arrows that are used to increase or decrease a time interval) with the support of a screen 61 and a mute/rest button 52f to mute/rest operational and technical audible and visual alarms in case of any operational or technical errors.

A supportive device 50 has also a screen 61 to monitor operational parameters such as a running time, an ultrafiltration volume, conductivity readings of a contactless conductivity cell1 56a and a contactless conductivity cell2 56b and/or a difference of conductivity readings, an ammonium level via an ammonium level sensor 63, operational and technical errors and any suitable operational parameters. Said parameters are stored in a memory card inserted in a slot 73 to be uploaded to the dialysis electronic medical record (EMR) to guide a physician to manage, assess and customize the dialysis protocol and parameters and to also customize a fresh dialysate bag's content and sorbent bags' contents for each patient.

Furthermore, a supportive device 50 also comprises a set knob 53 that is used to set different operational modes with the help of a screen 61 and its soft keys. Said modes such as a pressure control mode is to automatically control a speed of a bi-directional rotary pump1 55 and a speed of a bi-directional rotary pump2 59 to achieve a transmembrane pressure (TMP) target across a semipermeable membrane tube 25a during the operation as experts in this industry understand.

Another operational mode is an ultrafiltration mode that utilizes a scal1 62 readings and scal2 66 readings also to automatically control a speed of a bi-directional rotary pump1 55 and a speed of a bi-directional rotary pump2 59 to achieve the ultrafiltration target during the operation as experts in this industry understand.

A third operational mode is a conductivity difference mode as in this mode a conductivity differences between a contactless conductivity cell1 56a measurements and a contactless conductivity cell2 56b measurements are used to control a supportive device 50's operation to achieve the conductivity target during the operation as experts in this industry understand.

The same is done with an isolated ultrafiltration mode as a set knob 53 with the help of a screen 61 and its soft keys is used to set an isolated ultrafiltration target to suck an excess water from a patient via controlling a speed and direction of rotation of a bi-directional rotary pump1 55 to exert a negative pressure across a semipermeable membrane tube 25a (artificial kidney) with the help of a rotary valve1 54 that closes a fresh dialysate path and opens a used dialysate path. Also, during said an isolation ultrafiltration mode, a bi-direction rotary pump2 59 stops to block an infusate path and a cleaning/refreshment path.

FIG. 4 also illustrates a rotary valve1 54 that is used to manage a dialysate inflow and outflow to and from a dialysate lumen 27 during the operation as when a bi-directional rotary pump1 55 rotates in a forward direction to pump a fresh dialysate from a dialysate bag 67 to a dialysate lumen 27 via a dialysate passageway 43b of a needle assembly 40, then a second needle 42, then a port cavity 31, then through dialysate passageways 35 within a port housing 30 to a dialysate lumen 27. During such operation, rotary valve1 54 opens a fresh dialysate path that is connected to a dialysate bag 67 and closes a used dialysate path that is connected to sorbent bags 64. On other side when a bi-directional rotary pump1 55 rotates in a reverse direction to suck a used dialysate (spent dialysate) from a dialysate lumen 27 and pump it out to sorbent bags 64, a rotary valve1 54 closes a fresh dialysate path and opens a used dialysate path. In this sucking phase of dialysate, a dialysate exits from a dialysate lumen 27 through dialysate passageways 35 within a port housing 30, then through a second needle 42 of a needle assembly 40, then through a dialysate passageway 43b of a needle assembly 40, then through an extension tube 44 to the tubing system as in FIG. 5 to sorbent bags 64. So, it is an opposite operation compared to the above dialysate pumping phase. As above, we can see that the dialysate is in fluid communication from a dialysate bag 67 until dialysate lumen 27.

Figure 5:
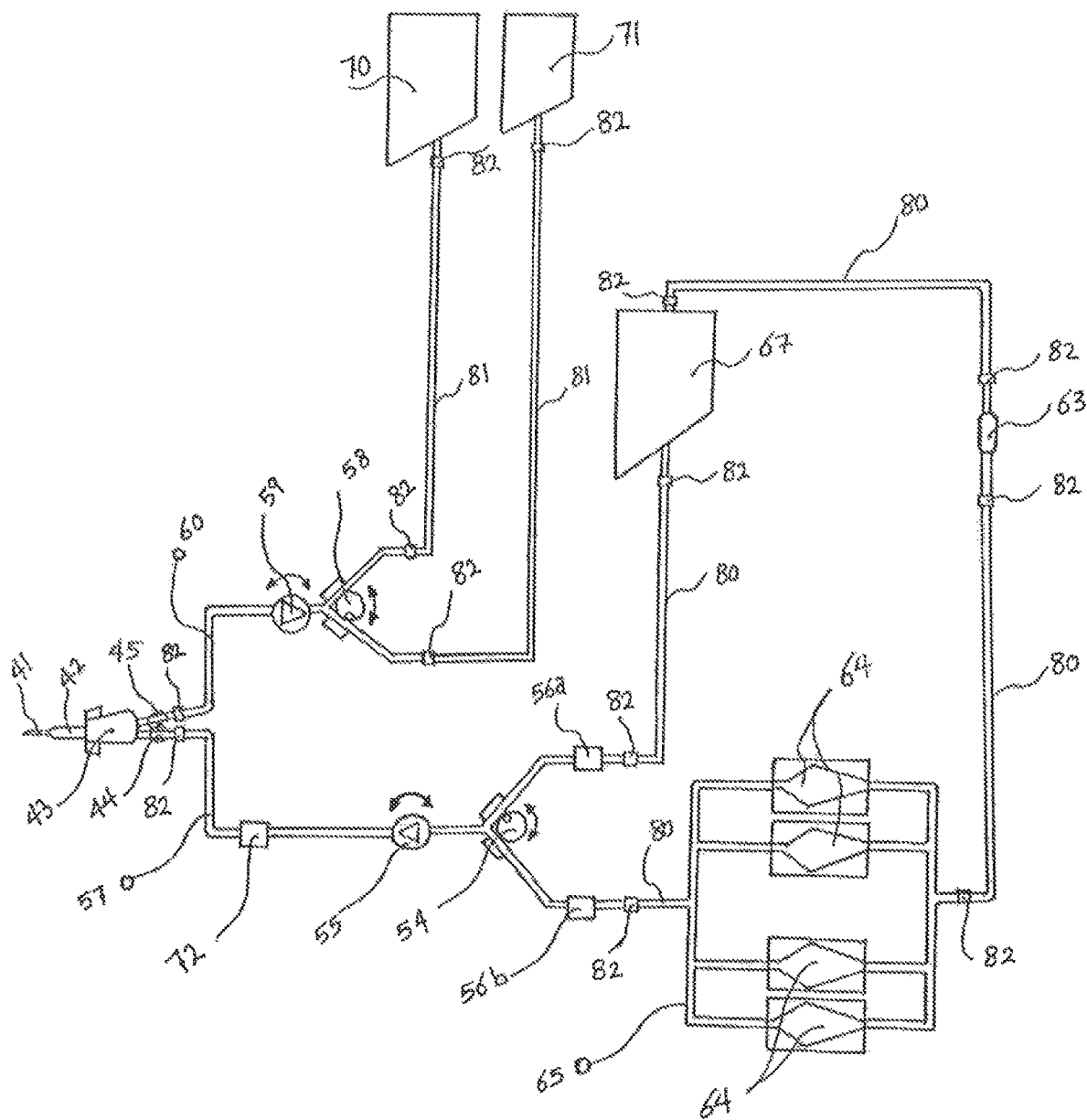
FIG. 5 is a schematic view of various components of the supportive device of FIG. 4 and its connecting tubing's.

On other side also a rotary valve2 58 is used to manage an infusate inflow and outflow to and from infusate/blood lumen 26 during the operation as when a bi-directional rotary pump2 59 rotates in a reverse direction to suck an infusate from infusate/blood lumen 26 and pump it out to an infusate bag 70 via a first needle 41 of a needle assembly 40 that is inserted inside an aperture 34 of a port housing 30 through a second septum 36, then through an infusate passageway 43c of a needle assembly 40 to an extension tube 45, then to the tubing system as in FIG. 5, then to an infusate bag 70. During such operation, a rotary valve2 58 opens an infusate path that is connected to infusate bag 70 and closes a cleaning path that is connected to a cleaning/refreshment solution bag 71.

In opposite, during a semipermeable membrane cleaning phase, a rotary valve2 58 opens a cleaning path that is connected to a cleaning/refreshment solution bag 71 and closes an infusate path that is connected to an infusate bag 70 to pump a cleaning/refreshment solution into a blood/infusate lumen 26 with the help of a bi-directional rotary pump2 59 that rotates in a forward direction to pump a cleaning/refreshment solution from a cleaning/refreshment solution bag 71 to a blood/infusate lumen 26 via the system of tubing as in FIG. 5, then to an extension tube 45 of a needle assembly 40, then to an infusate passageway 43c to a first needle 41, then through an aperture 34 and a second septum 36 to a blood/infusate lumen 26. So as we can see a cleaning/refreshment solution is in fluid communication with a blood/infusate lumen 26, i.e. cleaning/refreshment solution is in a fluid communication with a blood inside a blood/infusate lumen 26, so pushing a cleaning/refreshment solution into a blood/infusate lumen 26 acts to push a blood back to a vascular access (inferior vena cava as in FIG. 1 or any suitable vein or artery) via side openings 24 to clean a semipermeable membrane at the end of each dialysis session from any clotting that may occur during the operation.

The same process is applied in an infusate pumping phase to pumping an infusate from an infusate bag 70 to a blood/infusate lumen 26 via the system of tubing as in FIG. 5, then to an extension tube 45 of a needle assembly 40, then to an infusate passageway 43c to a first needle 41, then through an a aperture 34 and a second septum 36 of a port assembly 28 to a blood/infusate lumen 26. As we can see an infusate solution is in fluid communication with a blood/infusate lumen 26.

Also, in FIG. 4 a pressure sensor1 57 that is used to measure a pressure in a tubing that is used to inflow and outflow a dialysate to and from a dialysate lumen 27, a pressure sensor2 60 that is used to measure a pressure in a tubing that is used to inflow and outflow an infusate to and from a blood/infusate lumen 27 and a pressure sensor3 65 that is used to measure a pressure in a tubing that carries a used dialysate (spent dialysate) to sorbent bags 64. While, IV pole 69 is used to hang on an infusate bag 70 and cleaning/refreshment solution bag 71.

FIG. 4 also illustrates an ammonium level sensor 63 that is used to measure ammonium level in a dialysate solution at sorbent bags' 64 outlet and upon reaching a predetermined level, the treatment should be terminated or sorbent bags 64 (or partial of sorbent bags) should be replaced with fresh ones. An ammonium level sensor may be located inside a device cavity that includes sorbent bags 64. Also FIG. 4 illustrates a blood leak detector 72 that is used to detect a blood leak that may occur across a semibearable membrane's wall and in this case both bi-directional rotary pumps 55 and 59 stop and a rotary valve1 54 closes a dialysate path and a rotary valve2 58 closes an infusate path. In said case of a blood leak detection a supportive device 50 gives an audible and visual alarm on a screen 61. The same concept occurs with any other operational and technical errors.

A fresh dialysate bag 67 is in a range of about 0.2 liter (in case it is used with a wearable device that looks like a supportive device 50 but less in size to be adapted to be wearable and in this case there is no an IV pole 69) to about 5 liters based on each patient condition or any suitable size. The size of a fresh dialysate bag 67 is bigger than a fresh dialysate volume to accommodate for an ultrafiltration volume that is accumulated during the dialysis treatment.

Furthermore a pressure sensors 57 and 60 sense if a needle assembly 40 is still in its place inside a port housing 30 during the operation as in case a needle assembly 40 is not in its place inside a port housing 30, the pressure readings of pressure sensors 57 and 60 are going to be zero and in this case a supportive device 50 gives an audible and visual alarm on the screen 61 and both bi-directional rotary pumps 55 and 59 stop and a rotary valve1 54 closes a dialysate path and a rotary valve2 58 closes an infusate path for a patient safety.

It must be pointed out that the sorbent bags 64 are filed in another patent application belongs to the same inventor. The sorbent bags 64 contain sorbent materials selected from an Activated Carbone, a Urase, a Zirconium Phosphate, a Zirconium Oxide and Sodium Zirconium Carbonate or the like to regenerate and purify a used dialysate fluid. Such bags can be customized based on a patient condition and requirement.

Furthermore, sorbent bags 64 can be with different sizes, shapes, volumes, weights, densities, etc. These arrangements are based on each patient's need, condition, volume, size, etc. Further feature is, sorbent bags 64 can be connected in series or parallel to each other. Or sorbent bags 64 can be arranged with some bags are in parallel to each other and some bags are in series to each other or any arrangement for the best outcome for each patient.

FIG. 5 illustrates a schematic view of various components of a supportive device 50 of FIG. 4 and its connecting tubing's 80 (dialysate side) and 81 (infusate side) and connectors 82 wherein connecting tubing's 80 and 81 and a rest of component are connected as in FIG. 5, then before operation connecting tubing's 80 and 81 are primed by gravity to remove any air bubbles, then a needle assembly 40 is inserted into an aperture 33 of a port assembly 28 via a tissue tract 37a of a subcutaneous tissue 37 to connect a catheter 10 to the rest of components using extension tubes 44 and 45. On other side, the rest of components of a supportive device 50 in FIG. 5 are the same as in FIG. 4.

FIG. 6a illustrates one phase of operation wherein arrows 90a illustrate a blood when it enters inside a blood/infusate lumen 26 of a catheter 10 that has a catheter body 20 via side openings 24 at the same time an infusate solution exits a blood/infusate lumen 26 as per arrow 90b via an extension tube 45 of a needle assembly 40, a connector 82 that is created after a male connector 47 is connected to the system of tubing as in in FIG. 5 and a tubing 81. It must be pointed out that as above a blood and an infusate solution are in a fluid communication inside a blood/infusate lumen 26. So, sucking the infusate via bidirectional pump2 59, allows for the blood to be sucking from a vascular access and enters into a blood/infusate lumen 26 via side tubings 24. Also FIG. 6a illustrates an arrow 91a that illustrates a dialysate inlet into a dialysate lumen 27 via an extension tube 44 of a needle assembly 40, a connector 82 that is created after a male connector 46 is connected to the system of tubing as in in FIG. 5 and a tubing 80. It must be pointed out that as above a dialysate is in a fluid communication from a dialysate bag 67 to a dialysate lumen 27 through a system of tubing as in FIG. 5. As a dialysate flows from a dialysate bag 67, through the system of tubing as in FIG. 5, then through an extension tube 44 and a dialysate passageway 43b and a second needle 42 of a needle assembly 40, then through an aperture 33, a first septum 32, a port cavity 31, and dialysate passageways 35 of a port assembly 28 to dialysate lumen 27. So, sucking dialysate via bidirectional pump1 54 allows a dialysate to be sucked from a dialysate lumen 27. As we can see, a blood flow direction 90a and an infusate flow direction 90b are in the same direction, while they are on an opposite direction to a dialysate flow 91a across a semipermeable membrane of a semipermeable membrane tube 25a that acts as an artificial kidney of a catheter 10 to enhance the mass transfer across a semipermeable membrane. The rest of components in FIG. 6a are as in FIG. 2.

FIG. 6b illustrates another phase of operation wherein arrows 92a illustrate a blood when it exits out of a blood/infusate lumen 26 of a catheter 10 that has a catheter body 20 via side openings 24 while an infusate enters into a blood/infusate lumen 26 as per arrow 92b via an extension tube 45, a connector 82 and a tubing 81. Also FIG. 6b illustrates an arrow 91b that illustrates a dialysate exits outside a dialysate lumen 27 via an extension tube 44, a connector 82 and a tubing 80. As above, a blood flow direction 92a and an infusate flow direction 92b are in the same direction, while they are on opposite direction to a dialysate flow 91b across a semipermeable membrane of a semipermeable membrane tube 25a that acts as an artificial kidney of catheter 10 to enhance the mass transfer across a semipermeable membrane. The rest of components of FIG. 6b are as in FIG. 2.

A principal of operation that is designed to support the concept of a digital dialysis (CDD) in which a controlled pulsed blood flow and a controlled pulsed dialysate flow are used as follows: a new dialysis session starts via a rotation of a bi-directional rotary pump2 59 in a reverse direction for like 30 seconds (or any suitable time) to suck a cleaning/refreshment solution from blood/infusate lumen 26 of a catheter 10 that was used in a previous session to keep a semipermeable membrane clean and fresh and pump it out to a cleaning/refreshment solution bag 71 at the same time, a rotary valve2 58 opens a cleaning/refreshment solution path to a cleaning/refreshment solution bag 71 and closes an infusate path to an infusate bag 70.

As a supportive device memorizes the volume of a cleaning solution that was pumped at the end of a previous dialysis session, a bi-directional rotary pump2 59 rotates in a reverse direction and a rotary valve2 58 opens to facilitate a suction of the same volume and pump it out to a cleaning/refreshment solution bag 71 via a first needle 41 of a needle assembly 40 that is inserted inside an aperture 34 of a port housing 30 through a second septum 36, then through an infusate passageway 43c of a needle assembly 40 to an extension tube 45 to the tubing system as in FIG. 5 to an a cleaning/refreshment solution bag 71. Sucking a cleaning/refreshment solution that is in fluid communication with a blood allows for a blood to enter a blood/infusate lumen 26 via side openings 24 to cover a blood side of a semipermeable membrane area inside a semipermeable membrane tube 25a.

At the same time a bi-directional rotary pump1 55 rotates in a forward direction for like 30 seconds (the same time of removing a cleaning/refreshment solution phase) to pump out a dialysate solution from a dialysate bag 67 to a dialysate lumen 27 of a catheter 10 to cover a dialysate side of a semipermeable membrane area inside a semipermeable membrane tube 25a that acts as an artificial kidney. Also, at the same time a rotary valve1 54 opens a path for a fresh dialysate inflow and closes a path of a used dialysate (spent dialysate) outflow to facilitate the operation.

As we can see that at the end of a 30 second period, a blood covers one side of a semipermeable membrane tube 25a that acts as an artificial kidney and a dialysate covers the other side of a semipermeable membrane tube 25a on opposite direction. This represents an ideal situation for a dialysis to be in place to enhance the mass transfer across a semipermeable membrane of a semipermeable membrane tube 25a.

Then a bi-directional rotary pump1 55 rotates in a reverse direction for like another 30 seconds or any other suitable time to suck and pump out a used dialysate (spent dialysate) to sorbent bags 64 for refreshment and recycling. At the same time, a rotary valve1 54 rotates to close a fresh dialysate path and open a used dialysate path to facilitate the operation. Also, at the same time bi-directional rotary pump2 59 rotates in a forward direction for the same period (30 seconds) to pump out an infusate solution from an infusate bag 70 to a blood/infusate lumen 26. Also, at the same time a rotary valve2 58 opens infusate path that is connected to an infusate bag 70 and closes a cleaning solution path that is connected to a cleaning solution bag 71.

So, each dialysis cycle takes 60 seconds as both a blood and a dialysate fill out both side of a semipermeable membrane tube 25a (artificial kidney) in 30 seconds interval plus another 30 seconds interval to push a blood out into a blood access and a dialysate out into sorbent bags, so each dialysis cycle is 60 seconds interval or any suitable interval.

Each cycle and/or its interval may be changed based on each patient's condition and requirement, so a customized cycle and a customized interval are used to achieve the best dialysis outcome for each patient. These controlled pulsed cycles support the concept of digital dialysis (CDD) in which we used a controlled pulsed blood flow interval and a controlled pulsed dialysate flow interval to maximize the contact between a blood and a dialysate across a semipermeable membrane of a semipermeable membrane tube 25a that acts as an artificial kidney to enhance the mass transfer across a semipermeable membrane tube 25a to maximize the dialysis outcome for each patient.

Then a whole process is repeated for like 8 hours (or any suitable time) on a daily basis during night or at any suitable time for each patient.

As described above between dialysis sessions a blood/infusate lumen 26 of a semi-permeable membrane tube 25a fills with a cleaning/refreshment solution to clean any clotting that may occurs during dialysis and to keep a semipermeable membrane of a semipermeable membrane tube 25a always fresh.

Furthermore, a patient may use a syringe to pump in a cleaning/refreshment solution to clean a dialysate lumen 27 of a semipermeable membrane tube 25a and to keep a dialysate side of a semipermeable membrane also always fresh. This is done at the end of each dialysis session via discounting a connector 46 of a needle assembly 40 and re-connecting it to a suitable syringe with a cleaning/refreshment solution to push in a cleaning/refreshment solution to a dialysate lumen 27.

So, now both a blood/infusate lumen 26 and a dialysate lumen 27 across a semipermeable membrane tube 25a are covered by a cleaning/refreshment solution to always keeping a semipermeable membrane in both side clean and fresh. Furthermore, we appreciate the latest technology related to a semipermeable membrane material and construction as now there is a possibility to use an advanced semipermeable membrane with new features related to a biocompatibility and a blood coagulation such as patent no. CN105727771 A that reports "Heparinoid-modified polyvinyl alcohol hydrogel nano-compound hemodialysis film and preparation method thereof". As the nano-compound hemodialysis membrane of polyvinyl alcohol hydrogel layer has an outer layer that is heparinoid hydrogel context to enhance biocompatibility and minimize blood coagulation. Said patent is mentioned as a reference only.

Recently, several retrospective studies such as "A new polymethylmetacrylate membrane improves the membrane adhesion of blood components and clinical efficacy" an article that is published in a Renal Replacement Therapy Journal, Masakane et al., DOI 10.1186/s41100-017-0112-0, 2017, the findings indicate that platelet adhesion and activation were much lower by using a new PMMA membrane dialyzer Filtryzer NF. Those skilled in the art will recognize that this may ultimately improve a semipermeable membrane tube 25a's therapeutic outcome and enhance its lifetime.

Figure 7A:
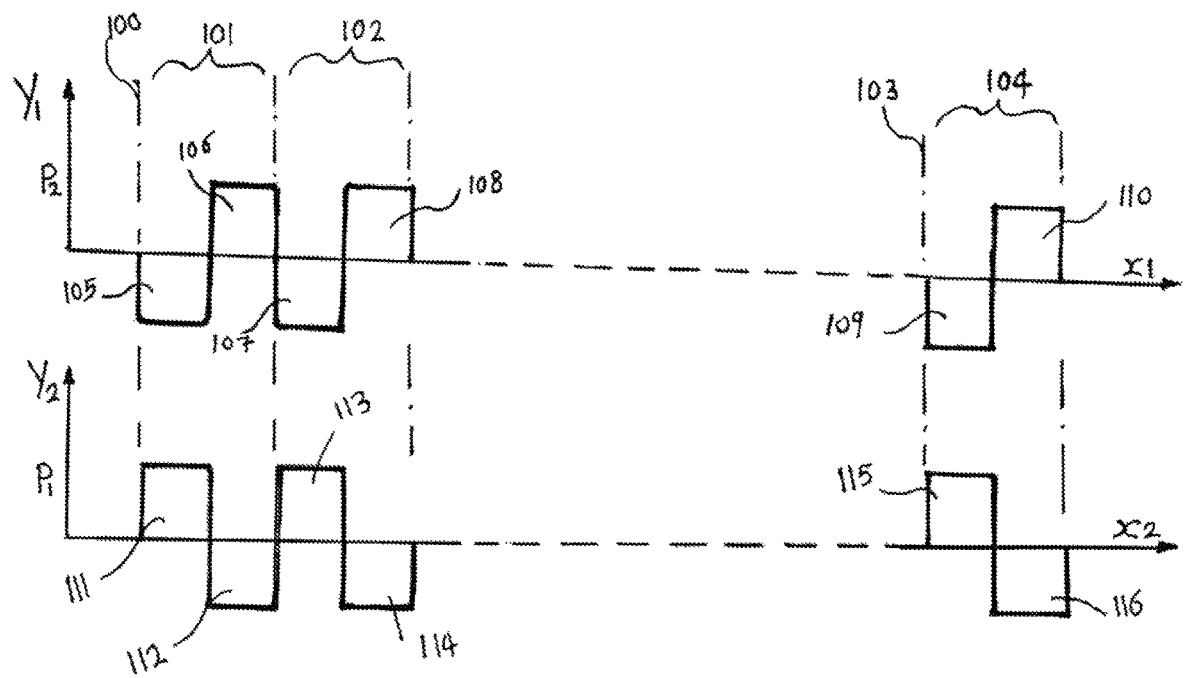
FIG. 7a illustrates one implementation of the operational cycles.

Based on the above concept of CDD, FIG. 7a illustrates one implementation of the operational cycles wherein y1-axis represents an operation of bi-directional rotary pump2 59 and x1-axis represents a time. While y2-axis represents an operation of bi-directional rotary pump1 55 and x2-axis represents a time. Each cycle may have 60 seconds interval or any suitable interval to maximize the contact time between a blood and a dialysate across a semipermeable membrane of a semipermeable membrane tube 25a as a suction phase may represent a 30 second interval and a pumping phase may represent another 30 second interval.

Also, in FIG. 7a the operational cycles of bi-directional rotary pump2 59 are as follows:
- 100—represents a start of a dialysis session.
- 101—represents a first cycle.
- 102—represents a second cycle.
- 103—represents a start of last cycle.
- 104—represents a last cycle.
- 105—represents a sucking phase of a cleaning/refreshment solution.
- 106—represents a pumping of an infusate solution.
- 107—represents a sucking phase of an infusate solution.
- 108—represents a pumping phase of an infusate solution;
- 109—represents a sucking phase of an infusate solution.
- 110—represents a pumping phase of a clean/refreshment solution.

Then, the operational cycles of bi-directional rotary pump1 55 are as follows:
- 111—represents a pumping phase of a dialysate solution.
- 112—represents a sucking phase of a dialysis solution.
- 113—represents another pumping phase of a dialysate solution.
- 114—represents another sucking phase of a dialysis solution.

115—represents a last pumping phase of a dialysate solution.
116—represents a last sucking phase of a dialysis solution.

Figure 7B:
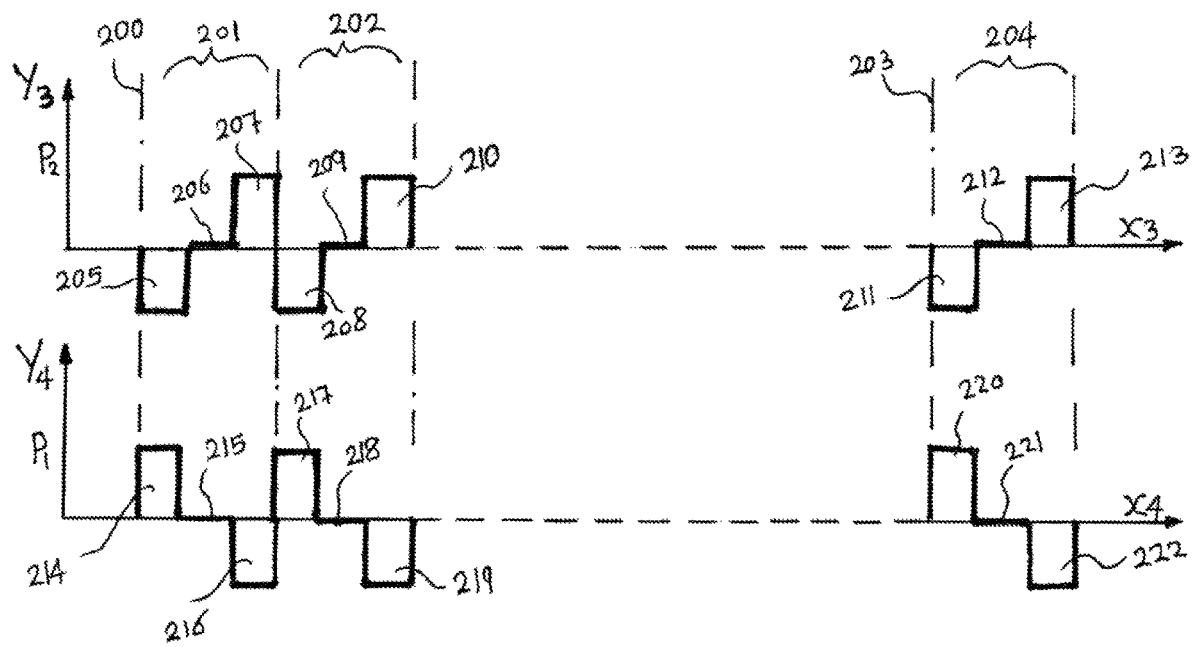
FIG. 7b illustrates another implementation of the operational cycles.

Also, to support the concept of CDD, FIG. 7b illustrates another implementation of operational cycles wherein y3-axis represents an operation of bi-directional rotary pump2 59 and x3-axis represents a time. While y4-axis represents an operation of bi-directional rotary pump1 55 and x4-axis represents a time. Each cycle may have a 60 second interval or any suitable interval. In these operational cycles, a suction phase may represent a 20 second interval, a dwell phase may represent a 20 second interval and a pumping phase may represent a 20 second interval. A dwell phase is selected again to maximize the contact time between a blood and a dialysate across a semipermeable membrane of a semipermeable membrane tube 25a to enhance the mass transfer across a semipermeable membrane.

Also, in FIG. 7b the operational cycles of bi-directional rotary pump2 59 are as follows:
200—represents a start phase of a dialysis session.
201—represents a first cycle.
202—represents a second cycle.
203—represents a start of a last cycle.
204—represents a last cycle.
205—represents a sucking phase of cleaning/refreshment solution.
206—represents a dwell time phase.
207—represents a pumping phase of an infusate solution.
208—represents a sucking phase of an infusate solution.
209—represents a dwell phase.
210—represents a pumping phase of an infusate solution.
211—represents a sucking phase of an infusate solution.
212—represents a dwell phase.
213—represents a pumping phase of a cleaning/refreshment solution.

Then, the operational cycles of bi-directional rotary pump1 55 are as follows:
214—represents a pumping phase of a dialysate solution.
215—represents a dwell phase.
216—represents a sucking phase of a dialysate solution.
217—represents a pumping phase of a dialysate solution.
218—represents a dwell phase.
219—represents a sucking phase of a dialysate solution.
220—represents a pumping phase of a dialysate solution.
221—represents a dwell phase.
222—represents a sucking phase of a dialysate solution.

The invention claimed is:

1. Artificial kidney and its supportive device comprising:
a catheter having an internal semipermeable membrane tube to act as an artificial kidney, the catheter comprising:
a proximal portion having the internal semipermeable membrane tube, a blood/infusion lumen, a dialysate lumen and side holes, wherein the internal semipermeable membrane tube is connected to a catheter tip, and wherein the side holes are in fluid communication with the blood/infusate lumen;
a distal portion having a dual septa port assembly, an inner tube, a blood/infusate lumen and a dialysate lumen;
a catheter body;
wherein said internal semipermeable membrane tube is located inside said catheter body around a guide wire insertion tube to create said blood/infusate lumen;
wherein said dialysate lumen is created between an external surface of said semipermeable tube and an internal surface of said catheter body;
and
a supportive device comprising: a device house with its cover that covers its internal cavity that includes a plurality of sorbent bags of different sizes, a screen, a plurality of buttons, a plurality of set knobs, a plurality of contactless conductivity cells, a plurality of bi-directional rotary pumps, a plurality of rotary valves, a plurality of pressure sensors, a slot for a memory card, a temperature sensor, a plurality of scales, an IV pole and a blood leak detector.

2. The artificial kidney and its supportive device of claim 1, further comprising:
a dialysate bag located on the supportive device's cover after it has been closed, an infusate bag and a cleaning/refreshment solution bag both are hanged on said IV pole, an ammonium level sensor that also located inside said supportive device's internal cavity.

3. The artificial kidney and its supportive device of claim 1, wherein said semipermeable tube and said inner tube have a same diameter and are connected together using a suitable connector.

4. The artificial kidney and its supportive device of claim 2, wherein said dual septa port assembly comprising:
a port housing that has a cylindrical shape and fixed on said catheter body after an insertion of said catheter;
a port cavity that has a conical shape;
a first septum that has a cylindrical shape is fixed inside said port housing;
a second septum is fixed inside said port house behind a first septum to create dialysate passageways on both sides internally of said port housing;
an aperture of said first septum is located under a subcutaneous tissue and guided by a tissue tract;
an aperture of second septum is located within said port cavity;
a blood/infusate lumen is located around a distal portion of the guidewire insertion tube and an internal surface of said inner tube; and
a dialysate lumen located between an external surface of said inner tube and an internal surface of said catheter body.

5. The artificial kidney and its supportive device of claim 4, further comprising a coaxial needle assembly comprising:
a first needle that has a smaller diameter and is positioned inside a second needle;
a second needle has a larger diameter with respect to the first needle;
a needle hub with a needle wing which acts as a needle stop after it has been inserted inside said port assembly;
a dialysate passageway located within said needle hub to be in a fluid communication with said dialysis lumen of said catheter; and
an infusate passageway which located within said needle hub to be in a fluid communication with said blood/infusate lumen of said catheter and is separated from said dialysate passageway within said needle hub; and
two extension tubes, one for blood/infusate and one for dialysate with male connectors and clamps.

6. A method of using the artificial kidney and its supporting device of claim 5 comprising steps of
inserting the catheter into a vein or artery;
using the supportive device to support, facilitate, and control operation of the artificial kidney, and to manage operational parameters; and using the supportive device to control dialysate inflow and outflow to and from the dialysate lumen, and to control blood/infusate inflow and outflow to and from the blood/infusate lumen across the internal semipermeable membrane tube.

7. The method of claim 6, further comprising a step of using a first of the plurality of rotary valves and a first of the plurality of bi-directional rotary pumps to control the dialysate inflow and outflow to and from the dialysate lumen during the operation.

8. The method of claim 7, further comprising a step of using a second of the plurality of rotary valves and a second of the plurality of bi-directional rotary pumps to control the blood/infusate inflow and outflow to and from the blood/infusate lumen during the operation.

9. The method of claim 8, further comprising a step of pumping fresh dialysate from a dialysate bag to the dialysate lumen via rotating the first of the plurality of bi-directional rotary pumps in a forward direction to pump the fresh dialysate from the dialysate bag to the dialysate lumen via the dialysate passageway of the coaxial needle assembly, the second needle, the port cavity, and dialysate passageways within the port housing.

10. The method of claim 9, further comprising a step of withdrawing spent dialysate from the dialysate lumen of the catheter to the plurality of sorbent bags by rotating the first of the plurality of bi-directional rotary pumps in a reverse direction to withdraw the spent dialysate from the dialysate lumen through the dialysate passageway within the port housing to the second needle of the coaxial needle assembly to the dialysate passageway of the needle assembly to the plurality of sorbent bags.

11. The method of claim 10, further comprising a step of withdrawing infusate/blood from the blood/infusate lumen of the catheter to an infusate bag by rotating the second of the plurality of bi-directional rotary pumps in a reverse direction to withdraw the blood/infusate from the blood/infusate lumen to the infusate bag via the first needle of the coaxial needle assembly that is inserted inside the aperture of the port housing, the second septum that is located behind the first septum, the blood/infusate passageway of the needle assembly, and extension tube.

12. The method of claim 11, further comprising a step of pumping infusate from the infusate bag to the blood/infusate lumen of the catheter by rotating the second of the plurality of bi-rotational rotary pumps in a forward direction to withdraw the infusate from the infusate bag via the coaxial needle assembly, the infusate passageway of the first needle, the aperture of the second septum of the port assembly to the blood/infusate lumen of the catheter.

13. The method of claim 12, further comprising a step of pumping cleaning/refreshment solution from the cleaning/refreshment solution bag to the blood/infusate lumen of the catheter at end of each dialysis session by rotating the second of the plurality of bi-directional pump in a forward direction to pump the cleaning/refreshment solution from the cleaning/refreshment solution bag via extension tube of the needle assembly, the infusate passageway of the first needle, and the aperture of the second septum of the port assembly.

14. The method of claim 13, further comprising a step of withdrawing the cleaning/refreshment solution from the blood/infusate lumen of the catheter and pumping the withdrawn cleaning/refreshment solution to the cleaning/refreshment solution bag at beginning of each dialysis session by rotating the second of the plurality of bi-directional rotary pumps in a reverse direction to withdraw the cleaning/refreshment solution from the blood/infusate lumen of the catheter and pump it to cleaning/refreshment solution bag via the first needle of the coaxial needle assembly that is inserted inside the aperture of the port housing through the second septum, the infusate passageway of the needle assembly, and extension tubing connected to the infusate bag.

15. The method of claim 8, further comprising a step of pressure control mode by the supporting device to automatically control speed of the first and second of the plurality of bi-directional rotary pumps to achieve a transmembrane target across the internal semipermeable membrane tube of the catheter during the operation.

16. The method of claim 8, further comprising a step of an ultrafiltration mode by the supporting device to automatically control speed of the first and second of the plurality of bi-directional rotary pump based on measured weights from the plurality of scales to achieve ultrafiltration target.

17. The method of claim 8, further comprising a step of conductivity difference mode to control operation of the supportive device by measuring conductivity difference between the plurality of contactless conductivity cells to achieve conductivity target during the operation.

* * * * *